(12) United States Patent
Lardieri

(10) Patent No.: US 6,315,013 B1
(45) Date of Patent: Nov. 13, 2001

(54) SYSTEM FOR ENSURING PERMANENT CONDITIONS OF STERILITY OF THE PRODUCT CONTAINED INSIDE A STRUCTURE THAT IS BEING CONNECTED TO ANOTHER STRUCTURE FOR TRANSFER

(76) Inventor: Salvatore Lardieri, Altopascio (IT)

( * ) Notice: Subject to any disclaimer, the term of this patent is extended or adjusted under 35 U.S.C. 154(b) by 0 days.

(21) Appl. No.: 09/559,482

(22) Filed: Apr. 27, 2000

(30) Foreign Application Priority Data

Aug. 27, 1999 (IT) ................................. PT99A0016

(51) Int. Cl.$^7$ ........................................ B65B 1/04
(52) U.S. Cl. ........................ 141/383; 141/301; 141/98; 141/DIG. 1
(58) Field of Search .................... 141/383, 386, 141/DIG. 1, 311 R, 301, 302, 305, 2, 18, 98

(56) References Cited

U.S. PATENT DOCUMENTS 5,988,951 * 11/1999 DiFrank et al. .................. 141/98
6,003,734 * 10/1999 Oh .................................. 222/146.6
6,056,027 * 5/2000 Patterson ........................ 141/370

* cited by examiner

Primary Examiner—Steven O. Douglas
(74) Attorney, Agent, or Firm—Young & Thompson

(57) ABSTRACT

A system for maintaining the sterility of the environment inside a device used to transfer pharmaceutical, food or similar products from one container to another. A special flange for fixing the gasket has been created that is fixed magnetically to the body of the container; a diaphragm inside the gasket completely closes the shaft's through hole that controls the distribution device, with the subsequent division of the shaft into two semi-shafts that are connected via the diaphragm by magnets hidden in the surfaces of the two facing semi-shafts. The bottom part of the distributor container and the top part of the transfer container are closed by two plates of ferrous magnetic material that is fixed to the parts by magnetic fittings, which plates will be extracted after the two containers are connected. Finally, a cylindrical screen is lifted up before the valve is activated to transfer the product in order to prevent any connection between the inner part of the connected containers and the extractor.

11 Claims, 7 Drawing Sheets

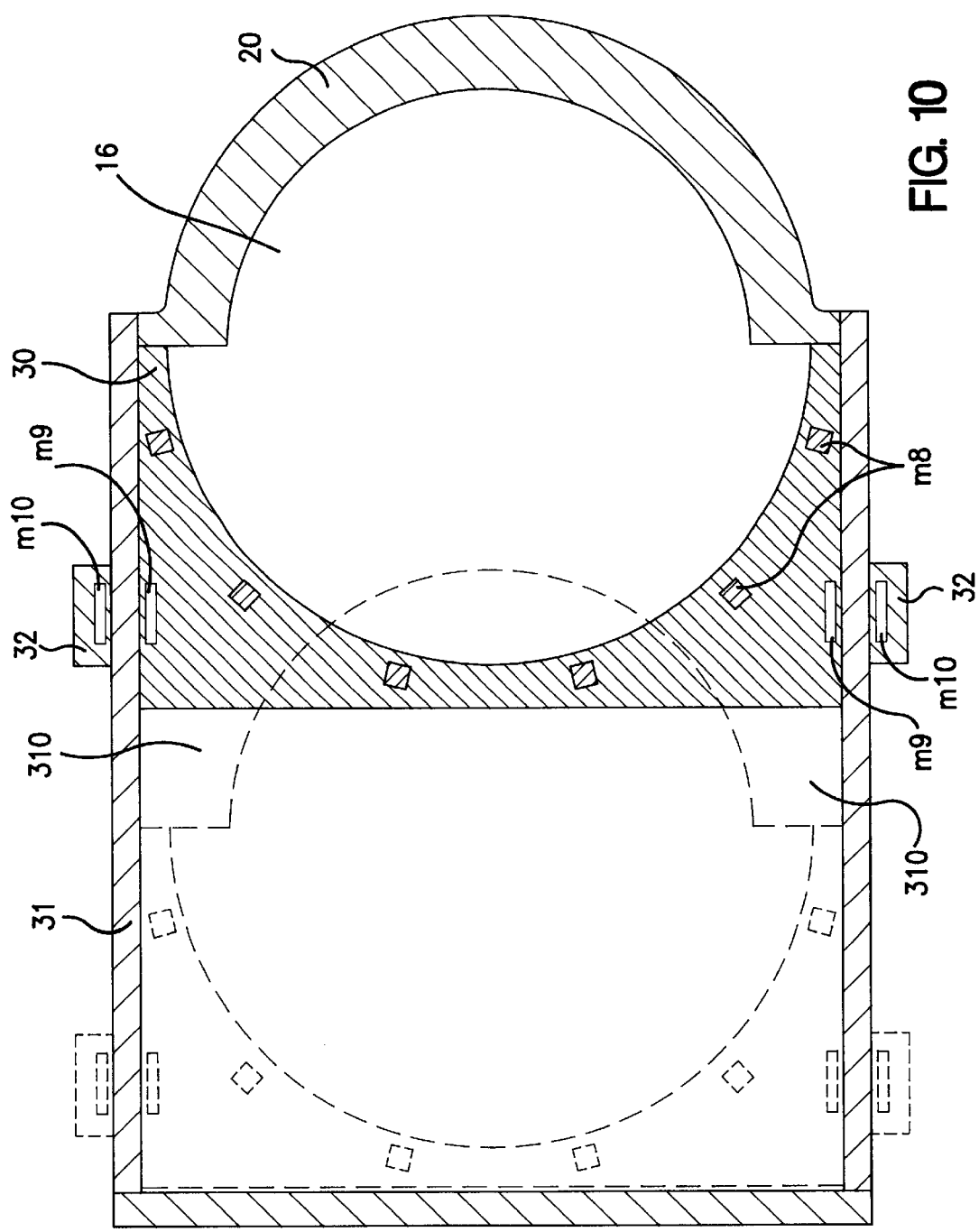
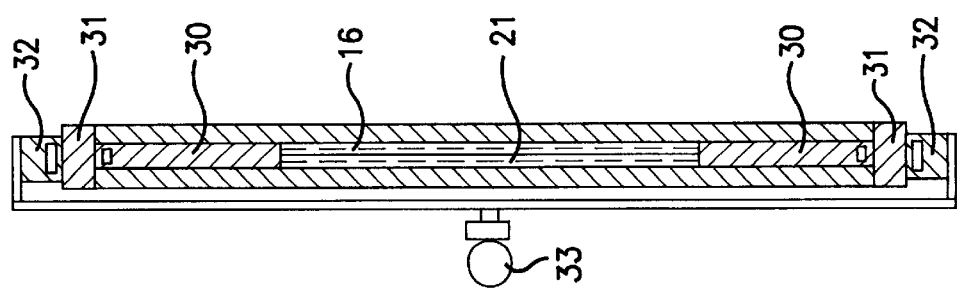

SYSTEM FOR ENSURING PERMANENT CONDITIONS OF STERILITY OF THE PRODUCT CONTAINED INSIDE A STRUCTURE THAT IS BEING CONNECTED TO ANOTHER STRUCTURE FOR TRANSFER

FIELD OF THE INVENTION

The invention is a system for ensuring the sterility of a container with a device for distributing or mixing pharmaceutical, food or similar products into another container that is also sterile whilst maintaining conditions of sterility during the operations of connecting the two containers with a cylindrical section, as the distribution device comprises a disk with an external diameter that is the same as the container's internal diameter, which disk can be rotated through 90° and which enables a change to be made from a horizontal closed position to a vertical open position by adjusting from the exterior a shaft that is connected to the disk. The invention also prevents toxic products from being expelled after the discharge process is terminated. The invention therefore addresses two very important aspects of the treatment of such products, namely:

a) maintenance of the sterility of the distributor container during the movements of the product distribution device;

b) elimination of any contact with the outside environment during connection of the two containers for product transfer.

BACKGROUND OF THE INVENTION

With regard to the first point, devices are currently made that have addressed the problem of sealing off the distribution disk during closing from the internal wall of the container by means of plastic material or by inserting a rubber gasket in the area in which the container wall comes into contact with the distribution disk. In both cases there are nevertheless seal problems in the area where the shaft joins the disk because it is controlled by an organ outside the container. In addition, if the seal is provided by a disk made of plastic material, clear wear problems arise, which are less marked in the case of seals provided by rubber gaskets, but the latter have to be frequently dismantled for cleaning, which is anyway necessary when the product being treated is changed, because of the fixing system of the gasket, which comprises fittings consisting of mechanical connecting organs on which dust often collects.

With regard to the second aspect, we have attempted to transfer material from one container to another without its coming into contact with the external atmosphere, by giving each of the two containers its own independent distribution organ. This ensures that the insides of the containers that are to be connected to one another are opened only after they have been connected. To protect the internal space between the connection sleeves and their valves from dust, dust caps are fitted to the sleeves, these caps, obviously, must be removed before connecting and this has the grave disadvantage of bringing the front spaces of the two containers into contact, albeit for a short time, with the external atmosphere and therefore making it possible for dust to settle.

In order to avoid this disadvantage a double-disk check device has been fitted: the check organ of the receiving container, by means of external control, is arranged with the bottom surface on the same level as the flange's connecting surface; the same thing happens with the top surface of the check organ of the transfer container in relation to the surface of its own connection flange, except that the latter does not have any control organ but carries out the rotary opening movement only if it is impelled by the other organ after the two containers have been connected. In this way the surfaces that have been contaminated by contact with the external atmosphere should not cause any disadvantages because they come into contact with one another and not with the internal atmosphere that thus remains sterile. This method of procedure nevertheless does not guarantee freedom from contamination, because contamination may arise, for example, from imperfect adherence of the two surfaces, which could cause, although to a minimal degree, dust to enter the inside of the containers.

SUMMARY OF THE INVENTION

The purpose of this invention is to introduce new devices in order to prevent the disadvantages that the two aspects of the problem that have been described.

The first aspect, as we have mentioned, is the imperfect seal of the valve body with the drive shaft and the complexity of the devices for dismantling the gasket for cleaning. For the first case the invention installs a diaphragm inside the gasket in order to completely shut off the shaft's through hole: the shaft consists of two sections, one outside the container and one inside, which are kept together by the force of magnets embedded in the surfaces of the semi-shafts facing one another.

For the second case a top fixing flange is provided for the gasket fixed to the body of the container by means of the attraction exercised by the magnets.

The second aspect is, as we have mentioned, the elimination of any contact with the outside environment whilst the two containers are connected together for the product transfer and is overcome by closing the bottom of the distributor container and the top part of the transfer container, by means of plates, appropriately fashioned, of magnetic ferrous material, fixed to the parts by magnetic fittings arranged on the surfaces of the aforementioned containers. During connection the surfaces of the two plates that have been contaminated by the outside environment come into contact. The connection between the two containers is established by removing the two plates with the help of an extractor. This enables the two containers to be connected without contaminating the internal environment with the external atmosphere. Finally, in order to prevent any contact between the internal parts of the containers and the internal part of the extractor, a cylindrical screen is fitted between the two parts that intervenes before the valve opens to transfer the material from one container to another.

DESCRIPTION OF THE DRAWINGS

FIG. 10 is a transversal section of an extractor according to the present invention.

FIG. 11 is a longitudinal section of the extractor shown in FIG. 10.

In order to provide complete information, there follows the description of a possible application that makes references to the attached drawings.

Figure 2:
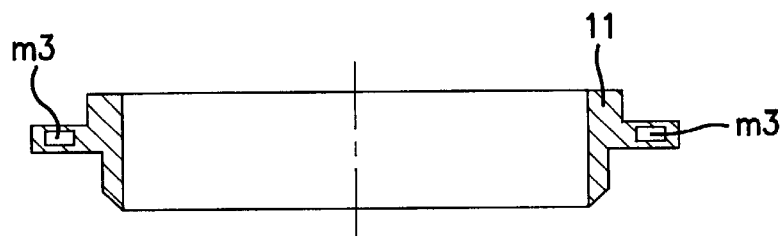
FIG. 2 is a flange shown in FIG. 1.
Figure 1:
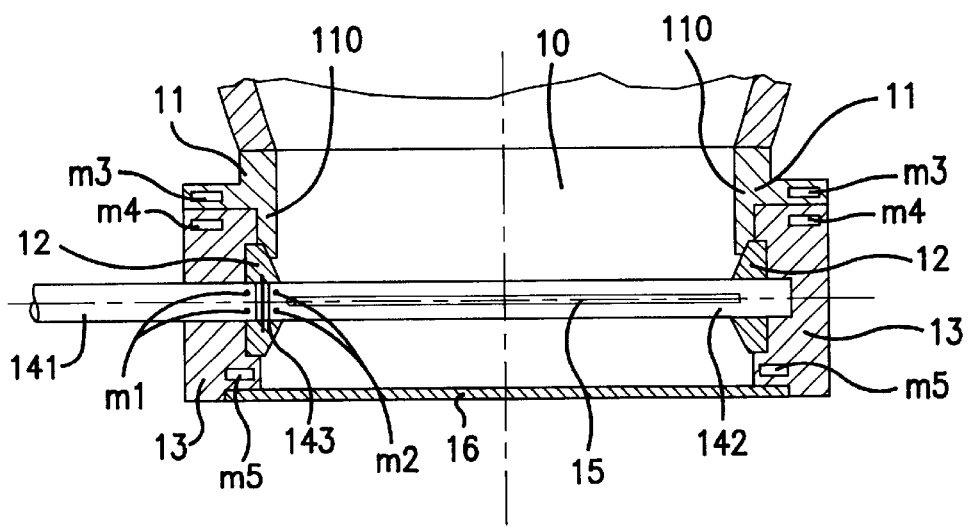
FIGS. 1, 3, 7, 8 and 9 are longitudinal sections of the device according to the present invention.
Figure 3:
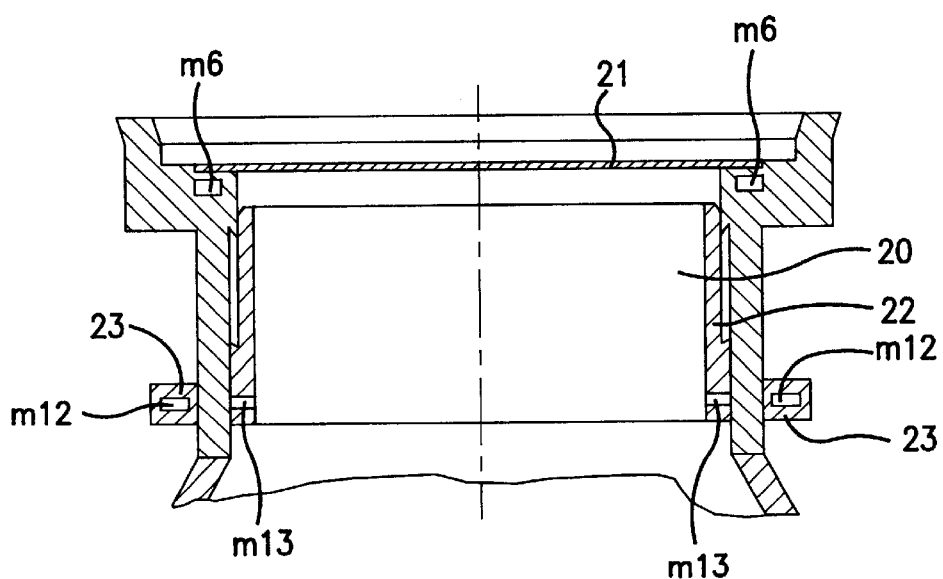
Figure 4:
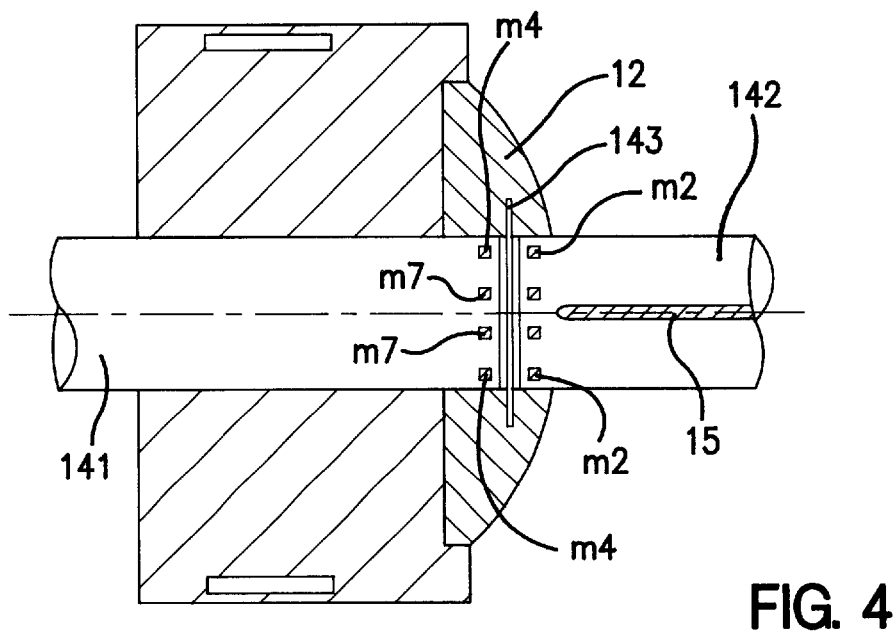
FIG. 4 is a magnified section of a valve body according to the present invention.

FIG. 1 shows a longitudinal section of the distributor container (10) showing the flange (11), which is also shown in FIG. 2, which is connected to the body of the distributor container (10) by the force of the magnets (m3), which are embedded in the flange (11) and the magnets (m4), which are embedded in the valve body (13). The action of the tooth (110) fixes the gasket (12) in an appropriately fashioned cavity in the valve body (13). The through shaft (140) that moves the valve (15) is divided into an external (141) and an internal (142) section, which are kept together by the force of attraction of the magnets (m1) and (m2) with opposite polarities, via the diaphragm (143), all of which is also shown in FIG. 4. This diaphragm is a true screen between the inside and the outside of the first container (10) in an area that must be considered to be critical for the seal, in view of the wear that the shaft (140) inflicts on the rubber gasket (12) in existing systems. The plate (16) of ferrous magnetic material closing the bottom of the distributor container (10) is also shown and is kept attached to its body by the magnetic force of the magnets (m5). FIG. 3 shows the corresponding longitudinal section of the transfer container (20) and shows the plate (21) in ferrous magnetic material that closes its opening, the plate is kept attached to its body, as well as to the cylindrical screen (22) by the magnetic force of the magnets (m6).

Figure 5:
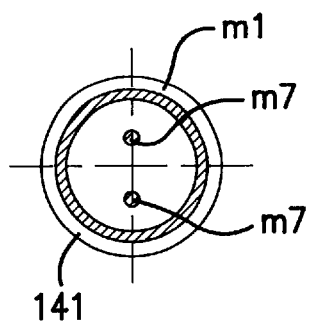
FIGS. 5 and 6 are traversal sections of a shaft according to the present invention.
Figure 6:
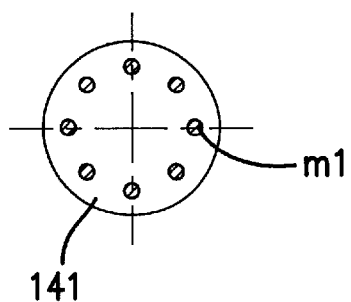

FIG. 4 shows a magnified section of the valve body (13) in the portion connecting the through shaft (140) and, in FIG. 5, the portion of the transversal section of the shaft (140) near the diaphragm (143). In this case the magnets (m1) are shown to consist of a single magnet in the form of a circular crown as opposed to the arrangement shown in FIG. 6. In the case of a single circular crown race a pair of magnets (m7) must be inserted to safety position the shaft.

Figure 7:
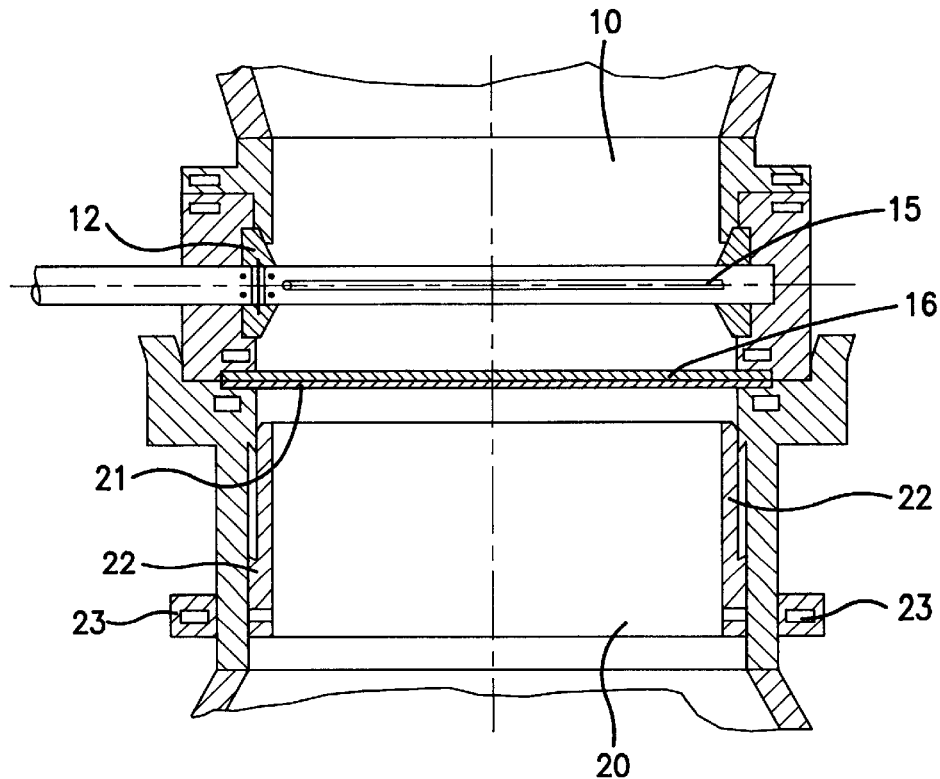
Figure 8:
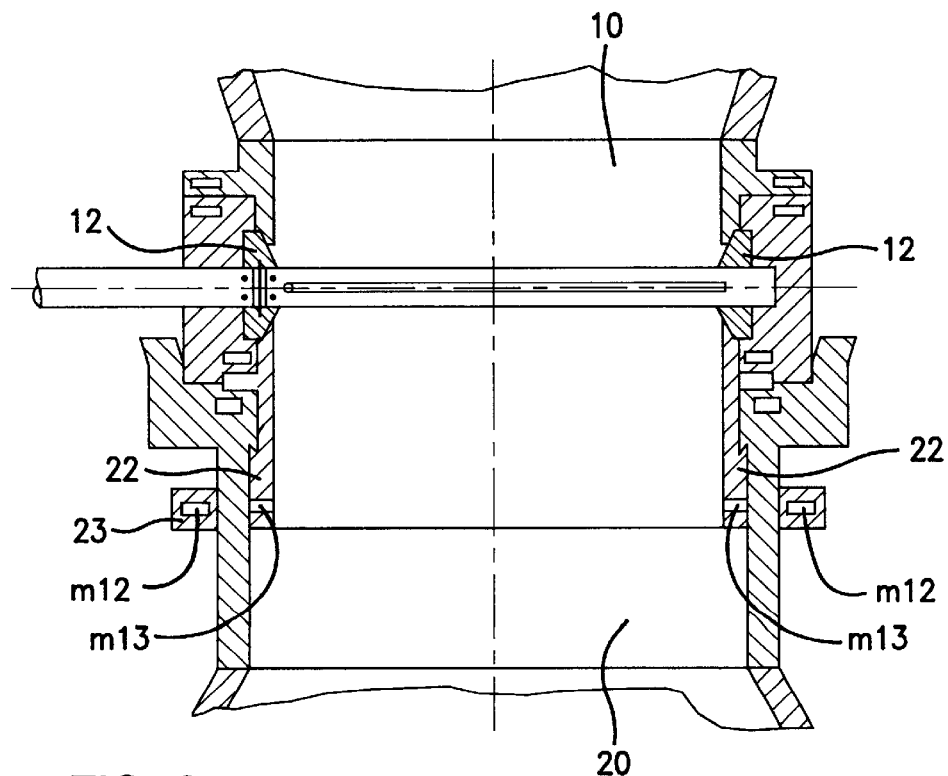

The drawings depict the two longitudinal sections of the two containers (10) and (20), which are connected in FIG. 7 with the two plates (16) and (21), which are still present, and in FIG. 8 after they have been extracted and the cylindrical screen (22) has accordingly moved upwards, which operations will be more fully described below.

Figure 9:
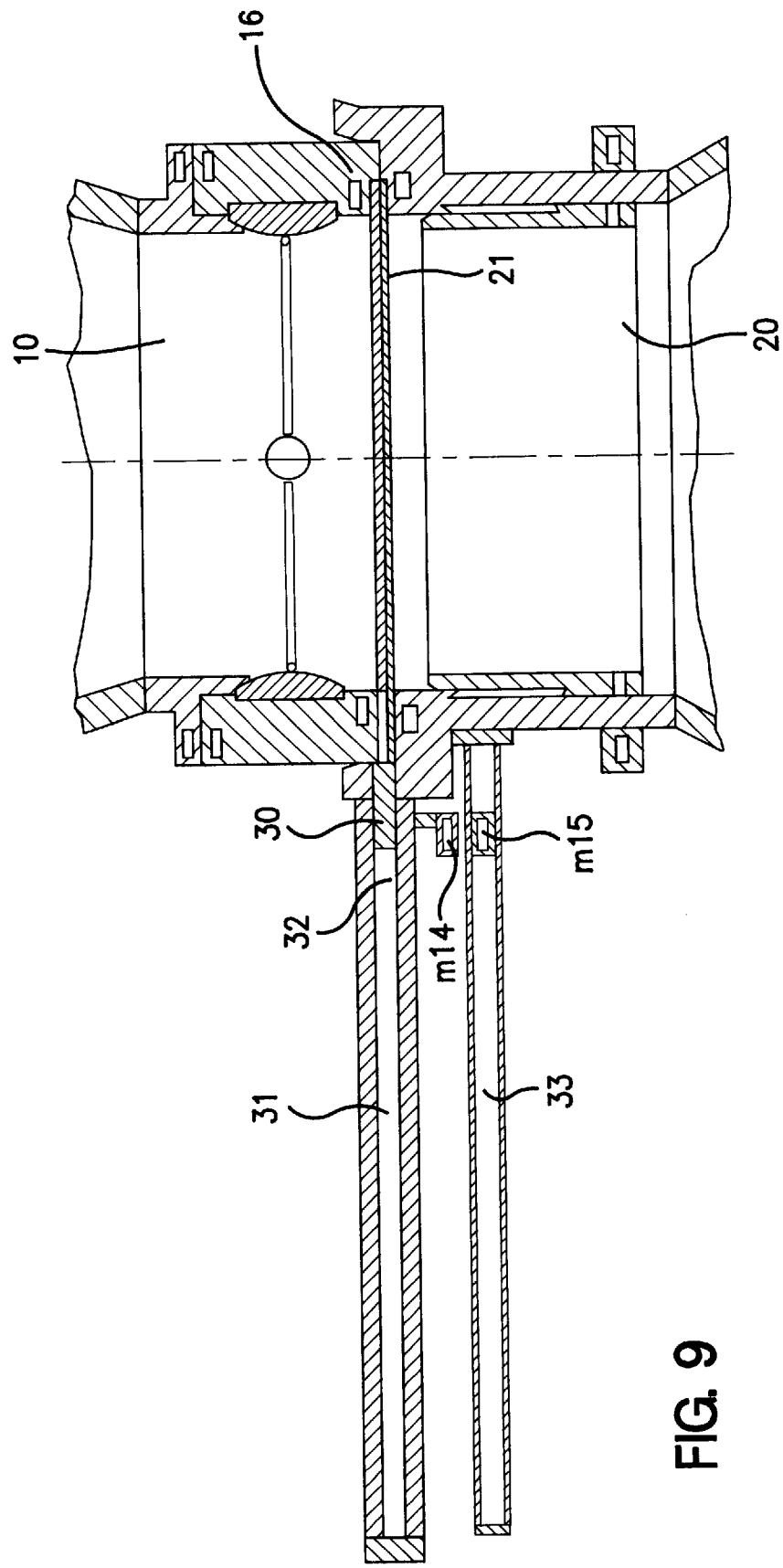

FIG. 9, shows a longitudinal section, which is normal in relation to those of the connected containers (10) and (20), with the plates (16) and (21) directly in contact and which are removed from their position to enable the two containers (10) and (20), to be connected by means of the action of the extractor, represented in FIG. 10 in the transversal section or, in FIG. 11, in the longitudinal section.

It consists of a plate (30) with a semicircular side, which perfectly reproduces that of the two plates (16) and (21), along the edge of which the magnets (m8) are arranged. Another two magnets (m9) are arranged on the two opposing straight sides. The plate (30) can run inside the container (31) that is connected to the outer wall of the transfer container (20). A device (32), outside the container (31) that can run along the walls of the container, contains, near the magnets (m9), two magnets (m10) with polarities that are the opposite of those of the magnets (m9). The device (32) can move, for example, if it is moved by a hydraulic cylinder (33).

Figure 12:
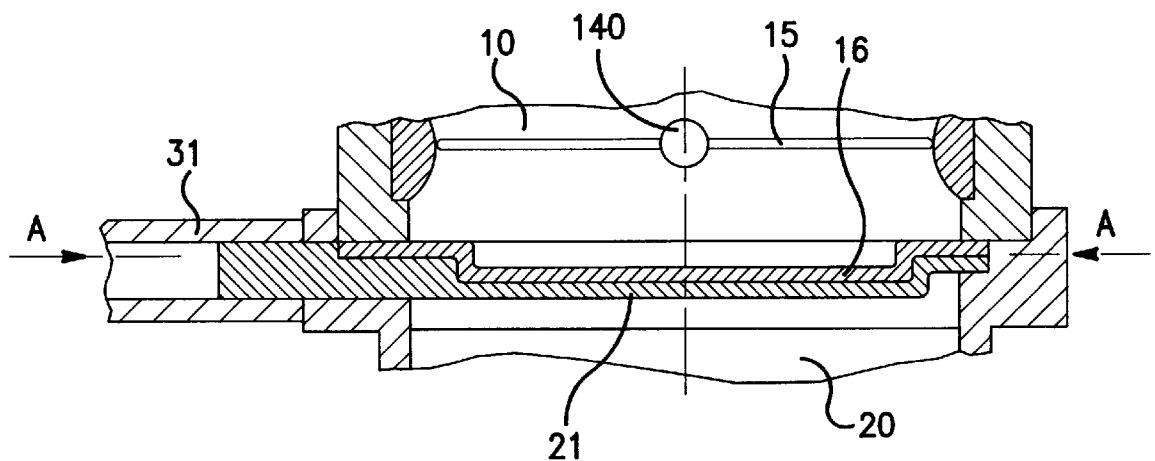
FIG. 12 is an alternate embodiment of the present invention.
Figure 14:
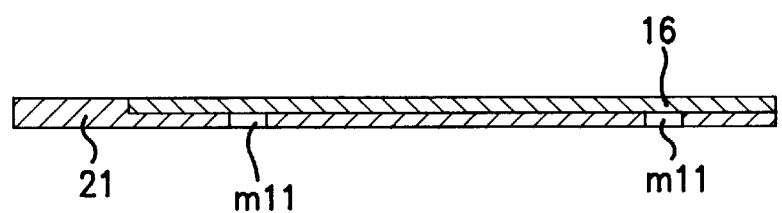
FIG. 14 is a plate arrangement of an alternate embodiment of the present invention.
Figure 13:
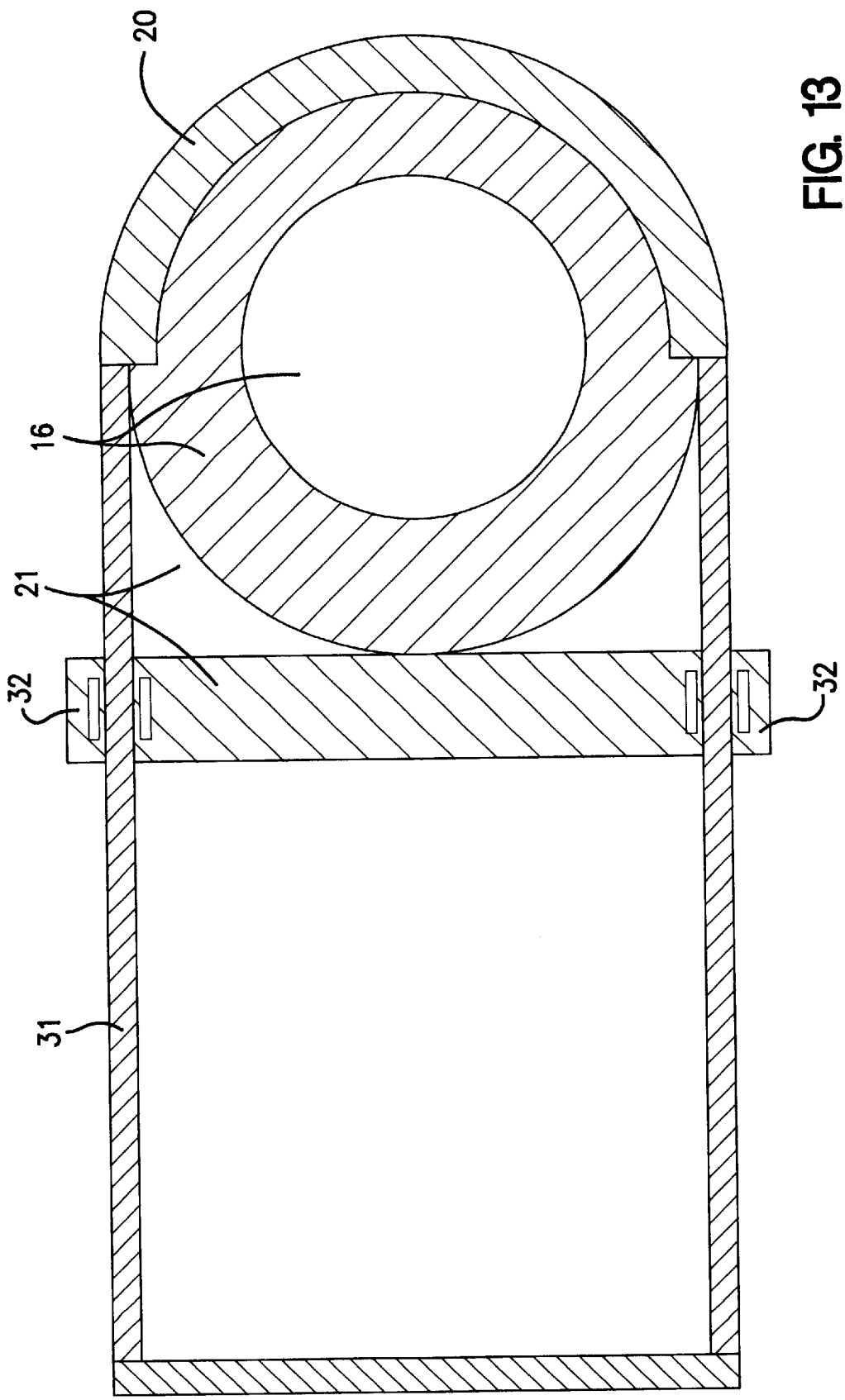
FIG. 13 is a traversal section of the embodiment shown in FIG. 12.

FIGS. 12–14 show another way of creating the plate-extraction plate, keeping this function for the plate (21). In this case the two plates do not have flat surfaces but a profile that, when they are connected, makes them fit into one another (FIG. 12), so that the plate (16) is dragged by the plate (21) as shown in FIG. 13. This result is also obtained by plates with a flat surface, maintaining the plate's (21) dragging function, placing magnets (m11) on the same plate in order for the two plates to link up, as indicated in FIG. 14.

It should be noted that the dimensions of the plates (16) and (21), and their perimeter profile, are such that apart from closing the connection between the two containers (10) and (20), they also perfectly cover the surfaces of the bodies of the containers themselves so that after the connection they continue to face each other without coming into contact.

The operation is the following: after transferring the distributor container (10) to the inside of the transfer container (20), the two plates (16) and (21) come into contact, are attracted by the permanent magnets (m8) and are thus connected to the plate (30). At this point, the cylinder (33), which is for example connected to the device (32) by the force of attraction exerted by the magnets (m14) and (m15), moves the device (32) and the movement of the device drags the plate (30) by means of the force of attraction exerted by the magnets (m10), with the internal magnets (m9), plate (30) will position itself inside the container (31) in such a way as to enable the two containers (10) and (20) to be connected. The same result is also obtained if it works as an organ that drags the plate (21).

As the links are made without through organs but with magnetic connections, it is easy to understand how the environment inside the two containers remains perfectly sterile and does not come into contact with the external environment, because the only contaminating surfaces, those outside the two closing plates (16) and (21), at the moment of connection, come into direct contact between themselves, remaining connected in a sterile environment (31) for the entire period of transfer of the material from one container to the other. The position assumed by the plate (30) with the two plates (16) and (21) is shown by the dotted line in FIG. 10, and is the same as that assumed by the two plates, if the plate (21) is used as a dragging element. We can now see how the area (310) inside the container (31) would be contaminated by the transfer of product during its transfer from one container to the other if it were not segregated from the environment (310) by the cylindrical screen (22) that moves upwards to the position shown in FIG. 8 with the end part in direct contact with the gasket (12), thus also helping to keep it in its seat before the valve is opened. The movement towards the top takes place by moving the ring (23) on the outside, which is shown in FIGS. 3, 7 and 8, whose movement drags the cylindrical screen (22) through the action of the magnets (m12) on the ring (23) and the magnets (m13), located on the screen (22)

After the product has been transferred, before the two containers are detached the opposite operation of lowering the cylindrical screen (22), and of transferring the plates (16 and (21) and closing the two containers (10) and (20) takes place. We need only add that the remarks on the extractor connected to the transfer container (20) apply even if the extractor is connected to the distributor container (10), either solution depending on the fact that one or the other of the containers can be moved.

What is claimed is:

1. In a system for ensuring permanent conditions of sterility of a product contained inside a first structure with a transfer device for transferring the product into a second structure while said first structure is connected to said second structure, said transfer device comprising a disk rotatable by 90° so as to pass from a closed horizontal position to an open vertical position by a shaft integral to the disk and passing through a passage hole through a seal gasket; the improvement which comprises a diaphragm for closing the passage hole of the shaft through the seal gasket; said shaft being divided into two sections which are connected to each other by a magnetic force exerted by magnets of opposite polarities acting through said diaphragm.

2. The system according to claim 1, wherein the first structure comprises a distributor container and the second structure comprises a transfer container; one of said containers structured and arranged to be inserted in the other for connection therebetween in order to be able to transfer the product from said one container to the other; said containers being sealed off from the outside environment by a first plate and a second plate of ferrous magnetic material; the first plate being fixed to close the bottom of the distributor container, the second plate being fixed to close the top of the transfer container; said plates being fixed to their respective containers by a magnetic force exercized by permanent magnets arranged on respective surfaces of the containers, which after having made contact and therefore been connected, will remain connected.

3. The system according to claim 2, wherein the first and second plates are adapted to be simultaneously removed and transferred to a sterile environment through the action of an extractor that is connected rigidly to the transfer container; said extractor comprising a third plate with a semicircular profile on one side, which reproduces that of the first and second plates; and a plurality of magnets disposed along an edge of said profile which use their magnetic force to link up the first and second plates.

4. The system according to claim 3, wherein the extractor comprises a third container connected to an outer wall of said transfer container, and a dragging device disposed outside the third container, that can run along the walls of the third container; said dragging device being connected to the third plate through a magnetic force produced between magnets which are connected to the dragging device, and magnets of appropriate polarity that are connected with the third plate.

5. The system according to claim 3, wherein the extractor comprises a third container connected to an outer wall of said transfer container, and a dragging device disposed outside the third container, that can run along the walls of the third container; said dragging device being connected to the second plate through a magnetic force produced between magnets which are connected to the dragging device, and magnets of appropriate polarity that are connected with the second plate.

6. The system according to claim 3, wherein the transfer container includes a cylindrical screen structured and arranged to move upwardly towards the top before opening a valve for transfer of product from the distributor container to the transfer container, thereby eliminating any contact of the product with the environment inside the extractor.

7. The system according to claim 6, further comprising a dragging element disposed outside the transfer container which can run along the walls of the transfer container, said dragging element being connected to the cylindrical screen by a magnetic force between magnets that are connected to the dragging element and magnets of the appropriate polarity that are connected to the cylindrical screen.

8. The system according to claim 2, wherein each plate has a profiled surface such that when connected, said plates fit into one another and are adapted to be simultaneously removed and transferred to a sterile environment through the action of an extractor.

9. The system according to claim 8, wherein each plate has a flat surface, and said plates once connected, remain connected because of a magnetic force exerted by magnets inserted in one of said plates.

10. The system according to claim 2, wherein the first and second plates are adapted to be simultaneously removed and transferred to a sterile environment through the action of an extractor that is connected rigidly to the distributor container.

11. The system according to claim 2, wherein the seal gasket is made of rubber, and is kept in a seat by a tooth of a flange that remains connected to a valve body by a magnetic force between magnets inserted in the valve body and magnets inserted in the flange.

* * * * *